United States Patent [19]

Khazaeli et al.

[11] Patent Number: 4,565,687
[45] Date of Patent: Jan. 21, 1986

[54] MONOCLONAL ANTIBODIES SPECIFIC FOR THE UNBOUND β SUBUNIT OF HUMAN CHORIONIC GONADOTROPIN

[75] Inventors: Mohammad B. Khazaeli; William H. Beierwaltes; Barry G. England, all of Ann Arbor, Mich.

[73] Assignee: The Reagents of the University of Michigan, Ann Arbor, Mich.

[21] Appl. No.: 321,578

[22] Filed: Nov. 16, 1981

[51] Int. Cl.$^4$ .................. C12N 15/00; G01N 33/54; A61K 43/00
[52] U.S. Cl. .......................... 424/1.1; 424/9; 424/85; 424/177; 260/112 R; 435/7; 435/68; 435/172.2; 435/240; 436/510; 436/518; 436/528; 436/536; 436/542; 436/548; 935/104; 935/107; 935/108; 935/110
[58] Field of Search .............. 424/1, 1.5, 9, 1.1, 424/177, 85; 436/518–546, 510, 548; 260/112 R; 435/4, 7, 68, 70, 172, 240, 948; 935/104, 107, 108, 110

[56] References Cited

U.S. PATENT DOCUMENTS 4,331,647  5/1982  Goldenberg ................ 424/1.1
4,361,544 11/1982  Goldenberg .................. 424/9

OTHER PUBLICATIONS

Beers, Philip C., Reproductive Immunology, pp. 21–28, (1981).
Khazaeli, M. B. et al., Endocrinology, vol. 109(4), pp. 1290–1292, (10-1981).
Miggiano, V. et al., Cancer Treatment Reports, vol. 63(7), p. 1214, Abstract 361, (7-1979).
Gupta, S. K. et al., Ind. J. Exp. Biol., vol. 18, pp. 1361–1365, (12-1980).
Muralidhar, K. et al., Fed. Proc., vol. 40(6), pp. 1595, 1597, Abstract 321, (6-1981).
Wahlström, T. et al., J. Histiochem, Cytochem., vol. 29 (7), pp. 864–865, (7-1981).
Schonherr et al., Dev. in Biol. Std., vol. 50, pp. 235–242, (1981).
Bosch, A. M. G., Prot. Biol. Fluids, vol. 29, pp. 837–842, (1981), (Chem. Abst. vol. 96 #215701).
Tanner P. Prot. Biol. Fluids, vol. 29, pp. 843–846, (1981), (Chem. Abst. vol. 97 #915e).
Berger P. et al., Immunobiology, vol. 160(1), p. 5, No. 7, (1981).
Beers, P. C., Mt. Sinai Journal of Medicine, vol. 47(5), pp. 528–534, (1980).
Khazaeli, M. B. et al., Sigand Quarterly, vol. 4(1), p. 40, (1981).
"Molecular Immunology", vol. 17(2), pp. 287–290, (2-1980), Ivanyi and Davies.
"Indian J. Experimental Biology", vol. 18, (12), pp. 1361–1365, (1980), Gupta and Talwar, (Chemical Abstract vol. 94 #101115n).
"Endocrinology" vol. 109(4), pp. 1290–1292, (1981), Khazaeli et al.
"Am. J. Physiology", vol. 238, E293–E305, (1980), Moyle et al., Cordered ILL).

Primary Examiner—Ben R. Padgett
Assistant Examiner—M. Moskowitz
Attorney, Agent, or Firm—Harness, Dickey & Pierce

[57] ABSTRACT

Hybrid-myeloma cells which produce monoclonal antibody specific to the β subunit of human chorionic gonadotropin and methods of use of the monoclonal antibody.

11 Claims, 4 Drawing Figures

MONOCLONAL ANTIBODIES SPECIFIC FOR THE UNBOUND β SUBUNIT OF HUMAN CHORIONIC GONADOTROPIN

BACKGROUND OF THE INVENTION

The present invention relates to hybrid-myeloma cells which produce monoclonal antibody specific to the β subunit of human chorionic gonadotropin and to methods of use of the monoclonal antibody. The antibody of the present invention distinguishes the β subunit of human chorionic gonadotropin even in the presence of intact human chorionic gonadotropin.

Myeloma cells from a mouse may be fused with lymphocytes from the spleen of a mouse immunized with a particular antigen to provide fused cells or hybrid-myeloma cells which are termed hybridoma cells. Hybridoma cells produce and secrete specific antibodies and are capable of rapid proliferation as well as indefinite maintenance. Furthermore, hybridoma cells can be manipulated by techniques applicable to animal cells in permanent culture. For example, individual cells can be cloned to provide progeny or clones which produce monoclonal antibodies each identically specific to a single antigenic determinant. Samples of the clones may be taken at any time and grown in culture or injected into animals for large scale production of a specific monoclonal antibody. Monoclonal antibodies produced in this way can be a versatile tool in a variety of areas including biological research and clinical medicine.

One problem researchers have encountered is that antisera produced from animals immunized with intact human glycoprotein hormones suffer from a lack of specificity for molecules within a species. The human glycoprotein pituitary hormones are composed of two dissimilar noncovalently bound α and β subunits. The α subunit is common among pituitary glycoprotein hormones within a species. In contrast, the amino acid composition of the β subunits are different and confer upon each glycoprotein hormone its unique biologic and immunologic activities. Antisera produced from animals immunized with intact glycoprotein hormones recognize determinant sites on both subunits and therefore suffers from a lack of specificity.

In accordance with the present invention, clone cells are provided which secrete antibody specific for the β-subunit of human chorionic gonadotropin. The monoclonal antibody has little or no cross reactivity with intact human chorionic gonadotropin or with other glycoprotein pituitary hormones and their β subunits in the range in which they would be expected to be present in serum. In addition, the present invention involves methods of use of the monoclonal antibody for tumor localization and/or treatment, affinity chromatography and determination of the structure of human chorionic gonadotropin.

DESCRIPTION OF THE PREFERRED EMBODIMENT

Figure 1:
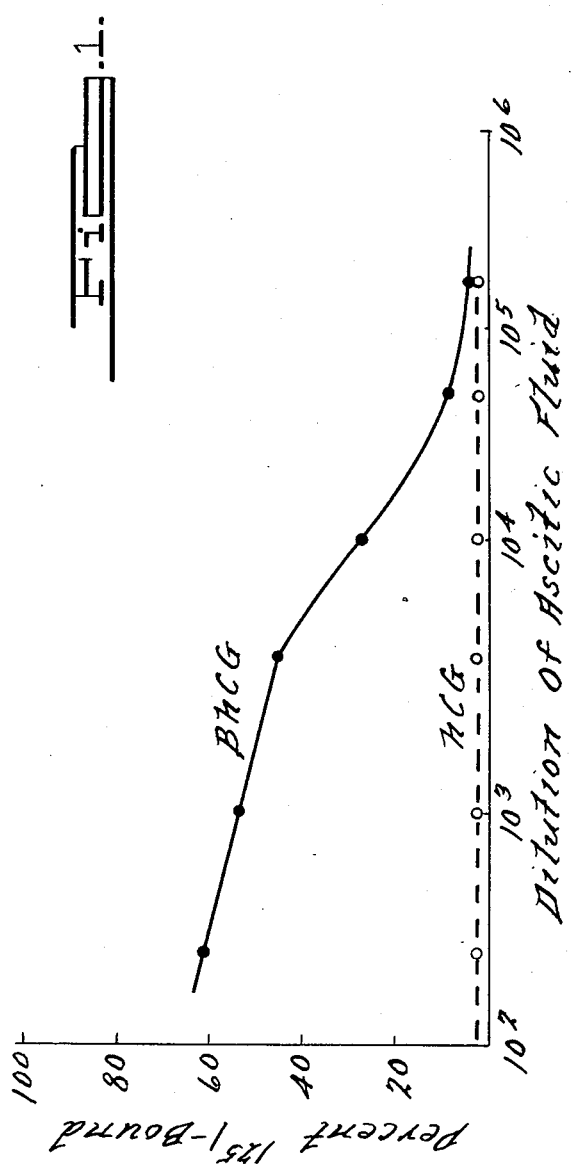
FIG. 1 is a graph showing the results of a time study of the monoclonal antibody of the present invention in ascitic fluid.

The hybridoma cell line of this invention has been named KEB-1E5.1 and has been deposited with American Type Culture Collection, 12301 Parklawn Drive, Rockville, Md. 20852. The date of deposit was Oct. 29, 1981, and the accession number given to the deposit by American Type Culture Collection was HB8095.

Generally speaking, the hybridoma cell line of the present invention is achieved in accordance with the following procedure. Laboratory mice are immunized with β-hCG and then serum tested for anti-hCG antibodies using Enzyme Linked Immunosorbent Assay (ELISA). Spleen cells of mice giving positive results to the test are then fused with a nonsecreting myeloma cell line. The resulting hybridomas are then tested for anti-hCG production using ELISA and titers are determined by radioimmunoassay. The culture media from positive hybridomas are diluted and tested for binding to radioisotope labelled hCG, β-hCG, FSH, TSH and LH. Selected hybrids are subcloned and antibodies are tested again for binding to the glycoprotein hormones. Monoclonal antibodies produced by the hybridoma cell line by the method described herein can be characterized in terms of binding kinetics and cross reactivity. More specifically, the hybridoma cell line of the present invention has been obtained as in the following Example.

EXAMPLE

An aqueous solution of purified β-hCG, obtained from Boehringer Mannheim, Indianapolis, Ind., was emulsified in an equal volume of complete Freund's adjuvant and 2.5 μg β-hCG was injected intraperitoneally into BALB/c mice. This primary immunization was followed by two secondary immunizations at three week intervals administered in the same manner except incomplete Freund's adjuvant was used. Serum samples were collected one week after the final immunization and tested for the presence of anti-β-hCG antibody (Titer check). When the titers confirmed the presence of anti-β-hCG antibodies, the mice were injected intravenously with 10 μg of β-hCG in 0.1 ml of distilled water. The spleens were removed three days later. The spleen cells were fused to nonsecreting myeloma cell line X63-Ag 8.653 using the fusion procedure of Gefter, et al., "A simple method for polyethylene glycol promoted hybridization of mouse myeloma cells," *Somatic Cell Genetics* 3:231 (1977) as modified by Claflin "Mouse myeloma-spleen cell hybrids: enhanced hybridization frequencies and rapid screening procedure" *Curr Top Microbil Immunol* 81:107 (1978). Enzyme Linked Immunosorbent Assay (ELISA) was performed following the procedures described by Engvall, et al. "Enzyme-linked immunosorbent assay, ELISA III. Quantitation of specific antibodies by enzyme labeled anti-immunoglobulin in antigen-coated tubes." *J. Immunol* 109:129, 1972. Purified hCG, from Boehringer Mannheim, Indianapolis, Ind., was adsorbed to the walls of 96 well cluster dishes following procedures described by Keren, "Enzyme-linked immunosorbent assay for immunoglobulin G and immunoglobulin A antibodies on *Shigella Flexneri* antigens," 1979, by adding 0.1 ml/well of a solution of 100 ng hCG/ml in 0.5M carbonate buffer (pH 9.6) and incubating for three (3)

hours at 37° C. The cluster dishes containing the antigen solution were then covered with parafilm and stored at 4° C.

Next the excess antigen was removed and the dishes washed four times with PBS containing 0.05% Tween 20 and 0.02% sodium azide (PTA). The supernatants from the hybridoma cultures were then diluted 1:20 in PTA. During experimentation 0.10 ml of this solution was added to the wells coated with antigen and to uncoated wells as a measure of non-specific adsorption. The dishes were then incubated at room temperature for four hours on a horizontal rotary shaker and the wells were washed four times with PTA. A solution (0.1 ml) containing alkaline phosphates conjugated to goat anti-mouse gamma globulin (GAMGG) was added to the wells. The reaction mixture was then incubated with agitation at room temperature for 18 hours. A further series of four (4) washes with PTA followed. After the washes, 1 mg of the substrate P-nitrophenyl phosphate disodium in 0.1 ml of 0.05M carbonate buffer, pH 9.8, containing 0.001M magnesium chloride was added to each well and the reaction was allowed to develop at room temperature for 30 minutes. Optical densities were then read on a Titertek Multiscan (Flow Laboratories Inc., Inglewood, Calif.) at 405 nm.

All radioimmunoassays were carried out utilizing the double-antibody technique of Midgley, "Radioimmunoassay: a method for human chorionic gonadotropin and human luteinizing hormone." *Endocrinology* 79:10, 1966. The assay was initially incubated at room temperature for one (1) hour. Timed studies confirmed equilibrium had been reached under conditions outlined above at about one (1) hour. A second antibody (GAMGG) in PBS containing 2.5% polyethylene glycol was added after one (1) hour incubation. Incubation was continued for a minimum of 30 minutes at room temperature. Separation of free hormone from antibody bound hormone was then accomplished by centrifugation. During experimentation, all assays were performed in duplicate. Intact glycoproteins used in the cross reactivity studies were: hCG (NIH RC 123), hFSH (NIH LER-1781-2), hTSH (NIAMDD hTSH-I-5) and hLH (NIH LER-1705). The β subunits used in cross reactivity studies were: β-hFSH (NIAMMDD N-596-C), β-hTSH (MIAMDD N-785-B) and β-hLH (LER 1793B).

The fusion between spleen cells and non-secreting myeloma cells resulted in 114 wells containing viable hybridoma cell lines. Initial screening of these hybridoma by ELISA techniques described above showed that 37 wells were producing anti-hCG antibodies. After a second seeding the culture media from the hybridomas were analyzed at 1:100 dilution for binding against $^{125}$I-hCG, $^{125}$-I-hFSH, $^{125}$I-hTSH and $^{125}$I-hLH. The results of this analysis are set forth in Table 1 below.

TABLE 1

TITER-CHECK OF HYBRIDOMA CELLS' MEDIA AT 1:100 DILUTION

| HYBRIDOMA | hCG | βhCG | LH | FSH | TSH |
|---|---|---|---|---|---|
| 1E2 | ++ | ++ | ++ | − | − |
| 1G2 | + | + | + | − | − |
| 1E5 | ++ | ++ | − | − | − |
| 1D7 | ++ | ++ | − | − | − |
| 1G10 | ++ | ++ | − | − | − |
| 1G11 | + | + | + | − | − |
| 2E7 | ++ | ++ | + | − | − |
| 2B9 | + | + | + | − | − |
| 3B4 | + | + | + | − | − |
| 3E4 | + | + | − | − | − |

TABLE 1-continued

TITER-CHECK OF HYBRIDOMA CELLS' MEDIA AT 1:100 DILUTION

| HYBRIDOMA | hCG | βhCG | LH | FSH | TSH |
|---|---|---|---|---|---|
| 3F7 | + | + | − | − | − |
| 3B8 | + | + | − | − | − |
| 4F3 | + | + | − | − | − |
| 4C4 | + | + | − | − | − |
| 4G5 | + | + | + | − | − |
| 4F9 | ++ | − | − | − | − |
| 4G10 | ++ | ++ | ++ | − | − |

+ Significant binding above non-specific binding
++ >10% binding above non-specific binding
− No binding The most promising hybridomas were subcloned and the subclones of a cell line (denoted as 1E5 cell line) were again tested for binding capacity to hCG, β-hCG, hFSH, hTSH and hLH. The binding of each of the hormones listed to the antibody derived from each subclone at 1:100 dilution of the culture media is depicted in Table 2 below.

TABLE 2

| | % BINDING | | | | |
|---|---|---|---|---|---|
| Cell Lines | hCG | βhCG | FSH | LH | TSH |
| 3.1E5.1 | 2.6 | 59.2 | 0 | 0 | 0 |
| 3.1E5.2 | 1.7 | 56.6 | 0 | 0 | 0 |
| 3.1E5.3 | 2.4 | 59.5 | 0 | 0 | 0 |
| 3.1E5.4 | 1.4 | 55.1 | 0 | 0 | 0 |

Titer-check of 1E5.1 Monoclonal antibodies in media at 1:100 dilution

As Table 2 depicts, the subclone 1E5.1 bound 59.2% of the $^{125}$I-β-hCG and displayed no binding capacity for any of the intact glycoprotein compounds. A sample of 1E5.1 cells were injected into the peritoneal cavity of BALB/c mice and the resulting ascitic fluid was collected for further study.

A titration curve was constructed by sequentially diluting ascitic fluid, collected as described above, in assay buffer and measuring the percentage of $^{125}$I-iodo-β-hCG and $^{125}$I-iodo hCG bound by the antibody. These percentages are reported in FIG. 1. The dilution of ascitic fluid required to give 50% maximal binding was calculated to be 1:75,000. This dilution of ascitic fluid was used in all subsequent characterization.

Figure 2:
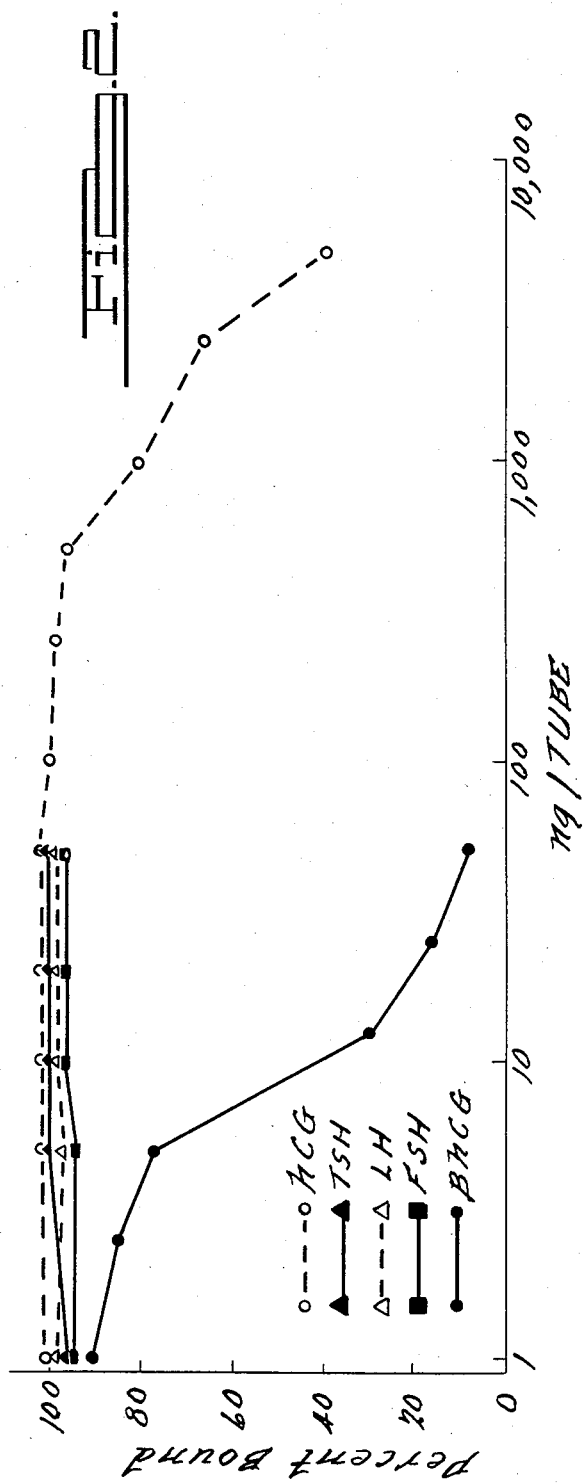
FIG. 2 is a graph showing the results of titration of the monoclonal antibody of the present invention in ascitic fluid.

Further, using double antibody radioimmunoassay, subclone 1E5.1 ascitic fluid obtained from 1E5.1 clone at 1:75,000 dilution was incubated with $^{125}$I-iodo β-hCG, hCG, hLH, hFSH and hTSH. The total assay volume was 1.0 ml. These intact glycoprotein hormones did not cross react with the antibody at the working range of the assay. The cross reactivity of hCG was calculated at 0.23%. The results of this cross reactivity analysis is shown in FIG. 2. The β subunit of hFSH, hTSH and hLH did not inhibit binding of $^{125}$I-β-hCG to the antibody at up to 250 ng/tube (not shown in FIG. 2).

Figure 3:
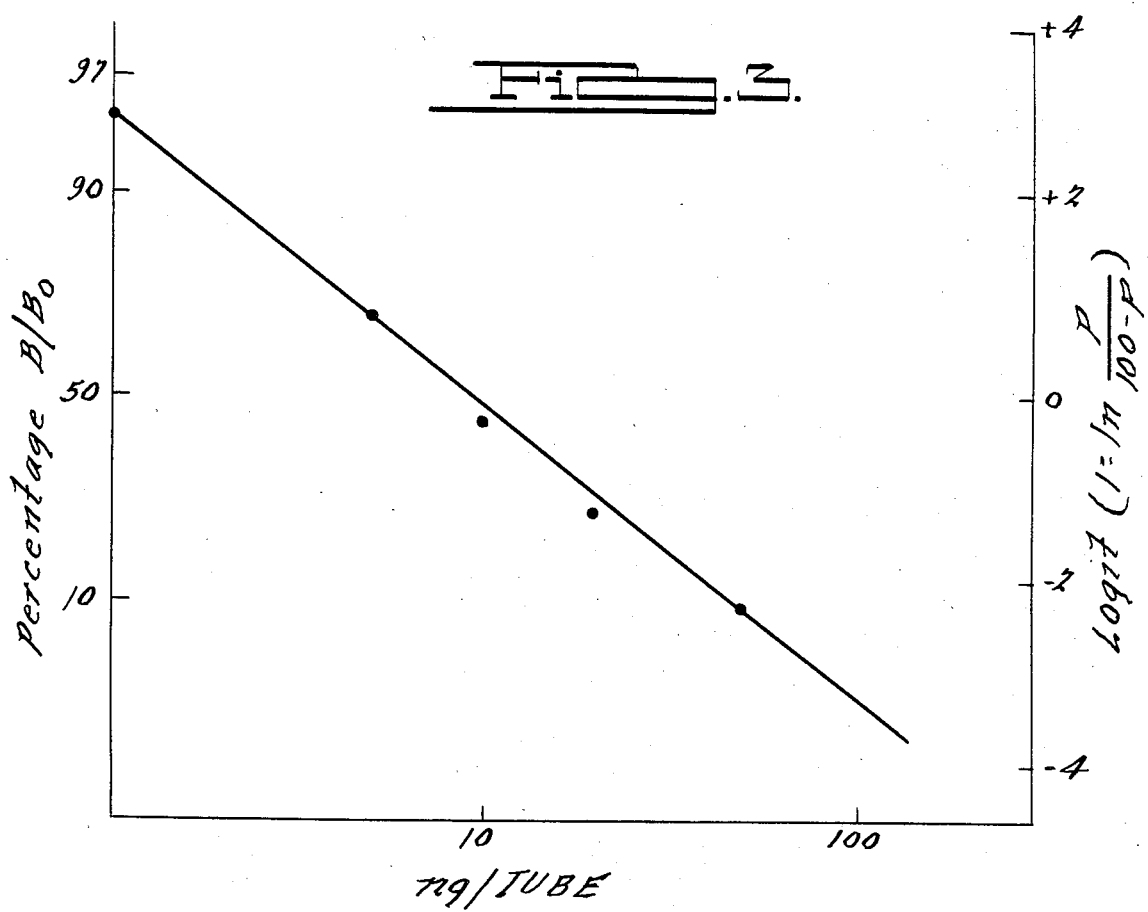
FIG. 3 is a graph showing the results of a cross reactivity check of the antibody of the present invention.

Using the double antibody radioimmunoassay, ascitic fluid obtained from 1E5.1 clone at 1:75,000 dilution was incubated with $^{125}$I-iodo-β-hCG in the presence of increasing concentrations of unlabelled β-hCG. The β-hCG inhibition curve is shown in FIG. 3. The slope of the curve was −3.2 on logit-log coordinates, and the sensitivity (defined as 2 SD from the buffer control) was about one (1) ng/tube.

Figure 4:
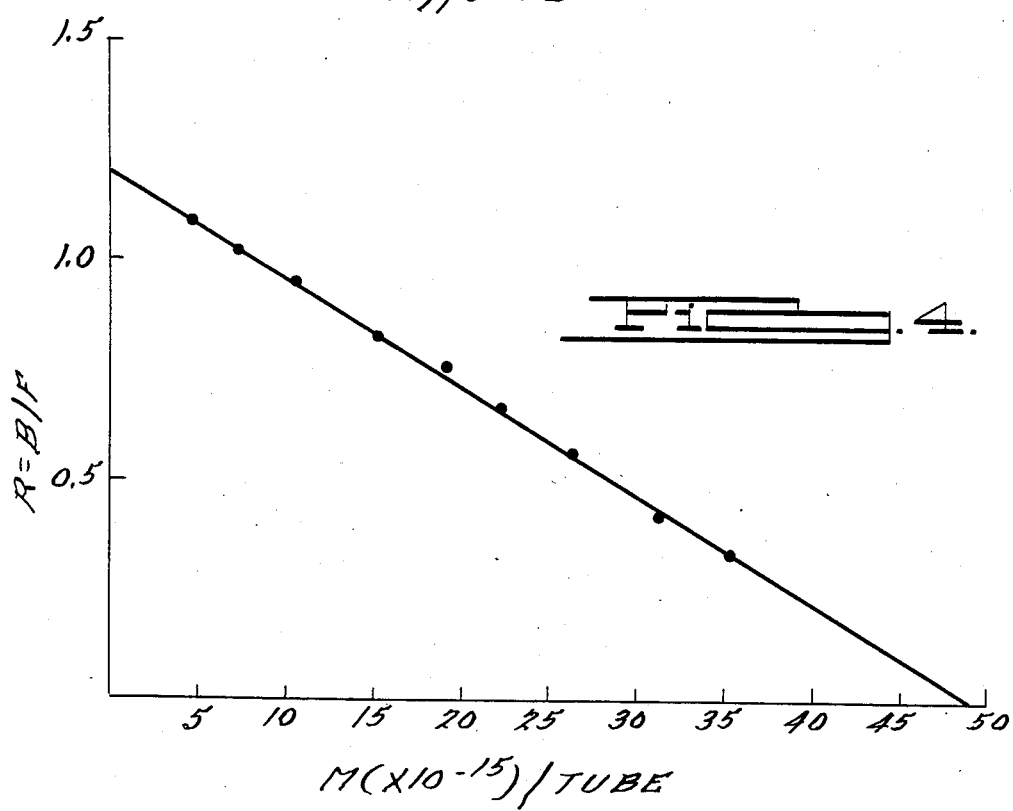
FIG. 4 is a graph showing the dose response curve of the antibody of the present invention in ascitic fluid.

Using the double antibody radioimmunoassay, ascitic fluid obtained from 1E5.1 monoclonal antibody at 1:75,000 dilution was incubated with increasing concentration of $^{125}$I-iodo-$\beta$-hCG. FIG. 4 sets forth the Scatchard plot after Rosenthal correction of the 1E5.1 monoclonal antibody. The dissociation constant ($K_d$), as determined by the Scatchard analysis with the Rosenthal correction for nonspecific binding was $3.3 \times 10^{-10}$M. Scatchard, "The attraction of proteins for small molecules and ions," Ann NY Acad Sci 51:660, 1949. Rosenthal, "A graphic method for the determination and presentation of binding parameters in a complex system," Anal Biochem 20:525, 1967.

The lack of cross reactivity of the $\beta$ subunits of other glycoprotein hormones indicates the antibody produced by the hybridoma subclone recognizes a determinant site that is unique to the $\beta$ subunit of hCG. Thus, in accordance with the present invention, a hybridoma cell line is obtained which produces monoclonal antibody specific to the $\beta$ subunit of human chorionic gonadotropin ($\beta$-hCG). The monoclonal antibody recognizes a determinant site that is unique to the $\beta$ subunit of human chorionic gonadotropin.

The monoclonal antibody of the present invention can be characterized by its binding characteristics and cross reactivity. These characteristics will be constant for all antibody from the hybridoma cell line of the present invention, unlike antisera from traditional animal sources.

A number of human malignant tissues and cultured cell lines secrete predominantly either $\alpha$ or $\beta$ subunits of hCG. The monoclonal antibody of the present invention provides means for a specific $\beta$-hCG assay procedure to simplify measurement of the level of $\beta$-hCG in sera and tumor extract of patients with malignancies. The assay results provide classification information in terms of $\beta$-hCG subunit secretion.

The monoclonal antibody of the present invention can be employed in affinity chromatography. In addition, the monoclonal antibody can be labeled with a radioactive isotope and employed to detect or localize tumors, and at higher doses to therapeutically treat tumors. The feasibility of combining nuclear medicine techniques with the use of radiolabeled antibodies to tumor specific antigens in order to facilitate the in vivo detection and localization of associated tumors has been extensively documented in both laboratory and clinical studies. The methodology, termed "radioimmunodetection," permits external imaging of tumors based on an increase in the tumor accumulation of radioactivity over normal tissues resulting from the specific antibody-antigen reaction.

The same methodology at higher dose levels may be used in treatment of those tumors which are rich in $\beta$-hCG. The methodology is further set forth in the following articles, which are specifically incorporated by reference herein: Quinones, J., Mizejewski, G., Beierwaltes, W. H.: "Choriocarcinoma scanning using radiolabeled antibody to chorionic gonadotrophin," J. Nucl. Med. 12:69, (1971); Beierwaltes, W. H.: "Radioiodine-labeled compounds previously or currently used for tumor localization," in Tumor Localization with Radioactive Agents, international atomic energy agency advisory group on tumor localization with radioactive agents, Vienna, Dec. (1974), IAEA-MG-50, pp. 47–56; Goldenberg, D. M. et al., "Use of Radiolabeled antibodies to carcinoembryonic antigen for the detection and localization of diverse cancers by photoscanning,"-N.E.J.M. 298:1384, (1978); Ballou, B. et al.: "Tumor location detected with radioactively labeled monoclonal antibody and external scientigraphy," Science 206:844, (1974).

What is claimed is:

1. A murine hybridoma produced by the fusion of a murine lymphocyte and a murine myeloma cell line that produces and secretes monoclonal antibodies of the IgG class that specifically bind to the unbound $\beta$ subunit of human chorionic gonadotropin in the presence of intact human chorionic gonadotropin.

2. A murine hybridoma produced by the fusion of a murine lymphocyte and a myeloma murine cell line that produces and secretes monoclonal antibodies of the IgG class that substantially specifically bind to the unbound $\beta$ subunit of human chorionic gonadotropin in the presence of intact human chorionic gonadotropin.

3. A murine hybridoma produced by the fusion of a murine lymphocyte and a murine myeloma cell that produces and secretes monoclonal antibodies of the IgC class that specifically bind to the unbound $\beta$ subunit of human chorionic gonadotropin in the presence of the $\beta$ subunits of human follicle stimulating hormone, human thyroid stimulating hormone and human luteinizing hormone as intact glycoprotein molecules.

4. A murine hybridoma produced by the fusion of a murine lymphocyte and a murine myeloma cell line that produces and secretes monoclonal antibodies of the IgG class that specifically bind to the unbound $\beta$ subunit of human chorionic gonadotropin having substantially no inhibition in said binding in the presence of unbound $\beta$ subunits of human follicle stimulating hormone, human thyroid stimulating hormone and human luteinizing hormone.

5. A murine hybridoma produced by the fusion of a murine lymphocyte and a murine myeloma cell line that produces and secretes monoclonal antibodies of the IgG class that specifically bind to the unbound $\beta$ subunit of human chorionic gonadotropin having substantially no cross reactivity with intact human luteinizing hormone, human thyroid stimulating hormone and human follicle stimulating hormone and less than 0.25% cross reactivity with intact human chorionic gonadotropin and having substantially no inhibition in said binding in the presence of unbound $\beta$ subunits of human follicle stimulating hormone, human thyroid stimulating hormone and human follicle stimulating hormone at up to 250 ng/tube.

6. The method of detecting a predominantly $\beta$-human chorionic gonadotropin ($\beta$-hCG) subunit secreting tumor in vitro, comprising: reacting unbound $\beta$-human chorionic gonadotropin ($\beta$-hCG) in sera with murine monoclonal antibody of the IgG class specific to said $\beta$-hCG in the presence of intact human chorionic gonadotropin and determining the amount of $\beta$-hCg-monoclonal antibody.

7. The method of detecting unbound $\beta$-human chorionic gonadotropin ($\beta$-hCG) by binding said unbound $\beta$-hCG to murine monoclonal antibody of the IgG class specific to said $\beta$-hCG in the presence of intact human chorionic gonadotropin by means of affinity chromatography and then determining the amount of $\beta$-hCG-monoclonal antibody.

8. The method of radioimmunodetecting a tumor secreting unbound $\beta$-human chorionic gonadotropin subunit ($\beta$-hCG) comprising contacting said tumor with radiolabeled murine monoclonal antibody of the IgG class specific to said unbound ($\beta$-hCG) in the presence of intact human chorionic gonadotropin and detecting the radioactivity emitted.

9. The method of therapeutically treating a tumor rich in unbound β-human chorionic gonadotropin subunits (β-hCG) comprising contacting said tumor with a therapeutic amount of radiolabeled murine monoclonal antibody of the IgG class specific to said unbound β-hCG in the presence of intact human chorionic gonadotropin.

10. The hybridoma cell line having the essential characteristics of hybridoma cell line KEB-1E5.1, deposited as ATCC HB8095, said characteristics consisting essentially of the production of murine monoclonal antibodies which specifically bind to the unbound β-human chorionic gonadotropin subunit in the presence of intact human chorionic gonadotropin and in the presence of the β subunit of human follicle stimulating hormone, human thyroid stimulating hormone and human luteinizing hormone.

11. A murine antibody of the IgG class that specifically binds to the unbound β subunit of human chorionic gonadotropin in the presence of intact human chorionic gonadotropin.

* * * * *

UNITED STATES PATENT AND TRADEMARK OFFICE
CERTIFICATE OF CORRECTION

PATENT NO. : 4,565,687
DATED : January 21, 1986
INVENTOR(S) : Khazaeli, et al.

It is certified that error appears in the above-identified patent and that said Letters Patent is hereby corrected as shown below:

| | | |
|---|---|---|
| Title page | | Assignee should be --Regents-- not "Reagents" |
| Column 6, | line 11, Claim 2 | "myeloma murine" should be --murine myeloma-- |
| Column 8, | line 7, Claim 11 | insert --monoclonal-- after "murine" |

Signed and Sealed this

Tenth Day of June 1986

[SEAL]

Attest:

Attesting Officer

DONALD J. QUIGG

Commissioner of Patents and Trademarks